US010238893B2

(12) United States Patent
Sloman

(10) Patent No.: US 10,238,893 B2
(45) Date of Patent: *Mar. 26, 2019

(54) DOSE RATE MODULATED STEREOTACTIC RADIO SURGERY

(71) Applicant: ELEKTA, INC., Atlanta, GA (US)

(72) Inventor: Brett Mathew Sloman, Chesterfield, MO (US)

(73) Assignee: Elekta, Inc., Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/485,204

(22) Filed: Apr. 11, 2017

(65) Prior Publication Data
US 2017/0216629 A1    Aug. 3, 2017

Related U.S. Application Data

(63) Continuation of application No. 14/472,317, filed on Aug. 28, 2014, now Pat. No. 9,656,099.

(51) Int. Cl.
*A61N 5/10*      (2006.01)

(52) U.S. Cl.
CPC ......... *A61N 5/1071* (2013.01); *A61N 5/1031* (2013.01); *A61N 5/1039* (2013.01);
(Continued)

(58) Field of Classification Search
CPC .. A61N 5/1071; A61N 5/1031; A61N 5/1039; A61N 5/1077; A61N 2005/1095
(Continued)

(56) References Cited

U.S. PATENT DOCUMENTS 6,546,073 B1   4/2003   Lee
8,278,633 B2   10/2012  Nord et al.
(Continued)

FOREIGN PATENT DOCUMENTS

CN    101848745 A    9/2010
EP    2266664 A1    12/2012
(Continued)

OTHER PUBLICATIONS

International Search Report and Written Opinion in corresponding International Application No. PCT/US2015/045662, dated Nov. 10, 2015, 10 pages.
"U.S. Appl. No. 14/472,317, Appeal Brief filed Jul. 8, 2016", 28 pgs.
"U.S. Appl. No. 14/472,317, Examiner Interview Summary dated Nov. 23, 2016", 3 pgs.
(Continued)

*Primary Examiner* — Nicole M Ippolito
*Assistant Examiner* — Hanway Chang
(74) *Attorney, Agent, or Firm* — Schwegman Lundberg & Woessner, P.A.; Sanjay Agrawal

(57) ABSTRACT

The present disclosure relates to methods and systems for radiotherapy. Embodiments of the present disclosure may receive a medical image including images of a target and an organ at risk (OAR). Some embodiments may also receive a target dose and a constraint on an OAR dose. Some embodiments may also generate a dose application plan based on the target dose and the constraint. Generation of the dose application plan may include determining a placement of an arc along which radiation is to be applied based on the target dose and a location of the target; dividing the arc into a plurality of segments; determining a dose rate associated with each segment; calculating a predicted OAR dose based on the determined dose rate; and comparing the predicted OAR dose with the constraint on the OAR dose to determine whether the predicted OAR dose satisfies the constraint on the OAR dose.

20 Claims, 10 Drawing Sheets

(52) U.S. Cl.
CPC .......... *A61N 5/1077* (2013.01); *A61N 5/1084* (2013.01); *A61N 2005/1095* (2013.01)

(58) Field of Classification Search
USPC .......................................... 250/492.1, 492.3
See application file for complete search history.

(56) References Cited

U.S. PATENT DOCUMENTS

| | | | |
|---|---|---|---|
| 9,656,099 B2 * | 5/2017 | Sloman | ................ A61N 5/1031 |
| 2003/0138077 A1 | 7/2003 | Lee | |
| 2010/0183120 A1 | 7/2010 | Nord et al. | |
| 2010/0219356 A1 | 9/2010 | Bzdusek | |
| 2012/0326057 A1 | 12/2012 | Remeijer et al. | |
| 2016/0059038 A1 | 3/2016 | Sloman | |

FOREIGN PATENT DOCUMENTS

| | | | |
|---|---|---|---|
| WO | WO 9014129 A1 | 11/1990 | |
| WO | WO-2016032798 A1 | 3/2016 | |

OTHER PUBLICATIONS

"U.S. Appl. No. 14/472,317, Final Office Action dated Dec. 21, 2015", 6 pgs.
"U.S. Appl. No. 14/472,317, Non Final Office Action dated Aug. 5, 2015", 6 pgs.
"U.S. Appl. No. 14/472,317, Non Final Office Action dated Oct. 20, 2016", 7 pgs.
"U.S. Appl. No. 14/472,317, Notice of Allowance dated Mar. 2, 2017", 7 pgs.
"U.S. Appl. No. 14/472,317, Response filed Jan. 12, 2017 to Non Final Office Action dated Oct. 20, 2016", 3 pgs.
"U.S. Appl. No. 14/472,317, Response filed Nov. 5, 2015 to Non Final Office Action dated Aug. 5, 2015", 6 pgs.
"International Application Serial No. PCT/US2015/045662, International Preliminary Report on Patentability dated Mar. 9, 2017", 8 pgs.
"Chinese Application Serial No. 201580046224.9, Office Action dated Dec. 5, 2018", w/o English translation, 7 pgs.

* cited by examiner

US 10,238,893 B2

DOSE RATE MODULATED STEREOTACTIC RADIO SURGERY

CROSS REFERENCE TO RELATED APPLICATION

This is a continuation of application Ser. No. 14/472,317, filed Aug. 28, 2014, the entire content of which is incorporated herein by reference.

TECHNICAL FIELD

This disclosure relates generally to radiation therapy or radiotherapy. More specifically, this disclosure is directed to systems and methods for dose planning in radiotherapy.

BACKGROUND

Radiotherapy is used to treat tumors in mammalian tissue, such as the brain. One such radiotherapy technique is Stereotactic Radiosurgery (SRS), by which a high dose of radiation is delivered with high precision over a short course of treatment to a lesion localized relative to a three-dimensional reference system. During SRS, multiple radiation beams are directed towards a target, such as a tumor, from different angles. These radiation beams converge at an isocenter. Tissue located at the isocenter receives a high dose while the surrounding areas receive relatively lower doses. Therefore, it is critical for an SRS system to deliver doses to a volume that conforms to the shape of the target. In this way, the target receives the required dose and the dose received by the surrounding tissue, often called the organ at risk (OAR), can be minimized.

In certain cases, the target may be surrounded by OARs that may be sensitive to radiation. As a result, the doses received by these OARs have to be limited to a predetermined level. Such limitations on the doses received by the OARs, often called constraints, need to be satisfied during treatment planning.

The constraints may be satisfied by manipulating the placement of the beam source. In an SRS system the beam source is often rotated along an arc, where the placement of the beam source is referred to as arc placement. In those instances where a tumor is close to critical OARs or where a tumor has a noncircular shape, manipulation of arc placement alone may not be able to satisfy the constraints.

One way of treating a noncircular or irregular shaped tumor is to combine multiple beam focus areas, also referred to as isocenters, into a noncircular or irregular shape that conforms to the shape of the tumor. FIGS. 1A-1C illustrate the concept of this method. As shown in FIGS. 1A and 1B, an isocenter (e.g., 10 or 20) associated with a group of arcs (e.g., arc group [12A, 12B] or [22A, 22B]) may have a circular (e.g., in a 2D image) or spherical (e.g., in a 3D image) shape. To map the elongated oval shape of a target 32 shown in FIG. 1C, isocenters 10 and 20 may be combined (e.g., by combining their associated groups of arcs) to form a combined isocenter (e.g., 30) that conforms to the shape of the target.

SUMMARY

Certain embodiments of the present disclosure relate to a radiotherapy system. The radiotherapy system may include a memory storing computer executable instructions and a processor device communicatively coupled to the memory. The processor device may be configured to execute the computer executable instructions for receiving a medical image of a patient. The medical image may include images of a target and an organ at risk (OAR). The processor device may also be configured to execute the computer executable instructions for receiving a target dose to be received by the target and a constraint on an OAR dose to be received by the OAR. In addition, the processor device may be configured to execute the computer executable instructions for generating a dose application plan based on the target dose and the constraint on the OAR dose. Generating the dose application plan may include determining a placement of an arc along which radiation is to be applied based on the target dose and a location of the target and dividing the arc into a plurality of segments. Generating the dose application plan may also include determining a dose rate associated with each segment and calculating a predicted OAR dose based on the determined dose rate associated with each segment. In addition, generating the dose application plan may include comparing the predicted OAR dose with the constraint on the OAR dose to determine whether the predicted OAR dose satisfies the constraint on the OAR dose.

Certain embodiments of the present disclosure relate to a method, implemented by a processor device, for dose planning in a radiotherapy system. The method may comprise receiving a medical image of a patient. The medical image may include images of a target and an organ at risk (OAR). The method may also comprise receiving a target dose to be received by the target and a constraint on an OAR dose to be received by the OAR. In addition, the method may comprise generating a dose application plan based on the target dose and the constraint on the OAR dose. Generating the dose application plan may include determining a placement of an arc along which radiation is to be applied based on the target dose and a location of the target and dividing the arc into a plurality of segments. Generating the dose application plan may also include determining a dose rate associated with each segment and calculating a predicted OAR dose based on the determined dose rate associated with each segment. In addition, generating the dose application plan may include comparing the predicted OAR dose with the constraint on the OAR dose to determine whether the predicted OAR dose satisfies the constraint on the OAR dose.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the invention, as claimed.

BRIEF DESCRIPTION OF THE DRAWINGS

The accompanying drawings, which constitute a part of this specification, illustrate several embodiments and, together with the description, serve to explain the disclosed principles.

DETAILED DESCRIPTION

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. And the singular forms "a," "an," and "the" include plural references unless the context clearly dictates otherwise.

Systems and methods consistent with the present disclosure are directed to Stereotactic Radiation Surgery (SRS), and in particular, to improve the flexibility and functionality of SRS technique in radiation treatment. In addition to controlling arc placement, embodiments of the present disclosure can divide a single arc into a plurality of segments or sub-arcs, and apply different dose rates for each segment. The radiation beam shape may also be controlled such that each arc may have different beam shapes. Systems and methods consistent with the present disclosure may also be used for other isocentric radiation treatments.

Figure 1A:
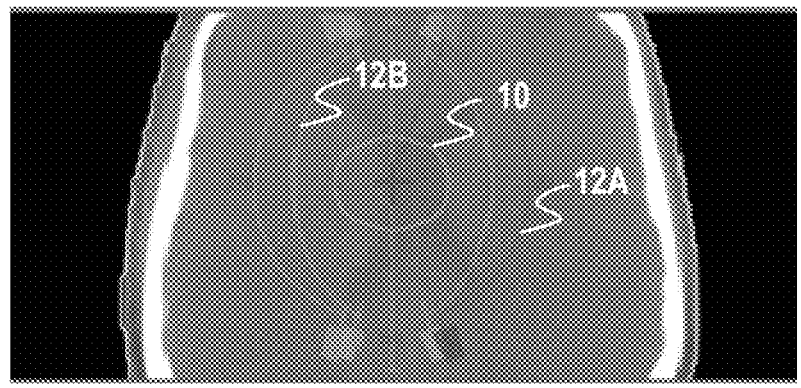
FIGS. 1A-1C illustrate a concept for combining isocenters.
Figure 1B:
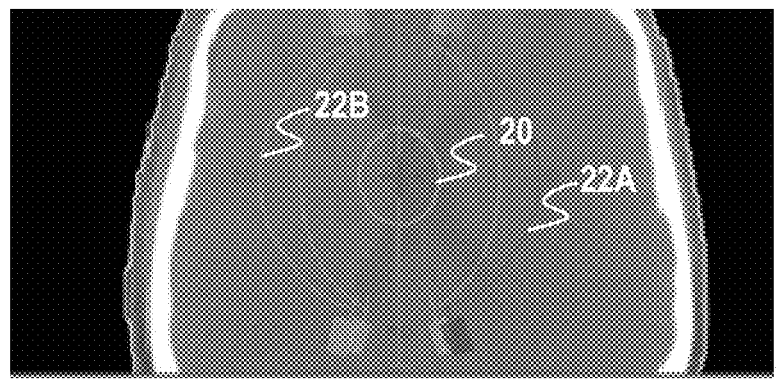
Figure 1C:
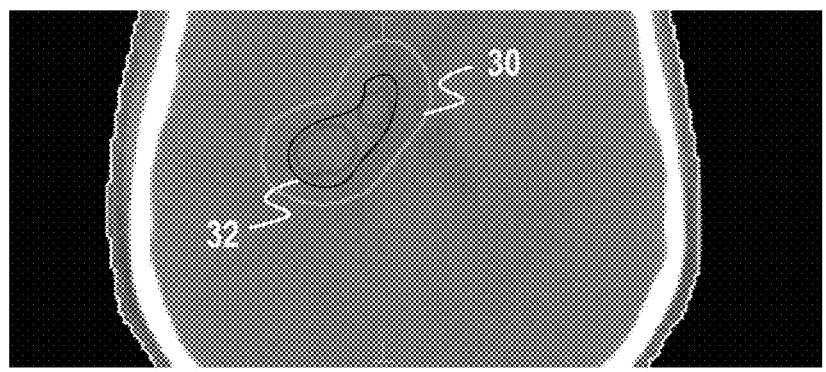
Figure 2A:
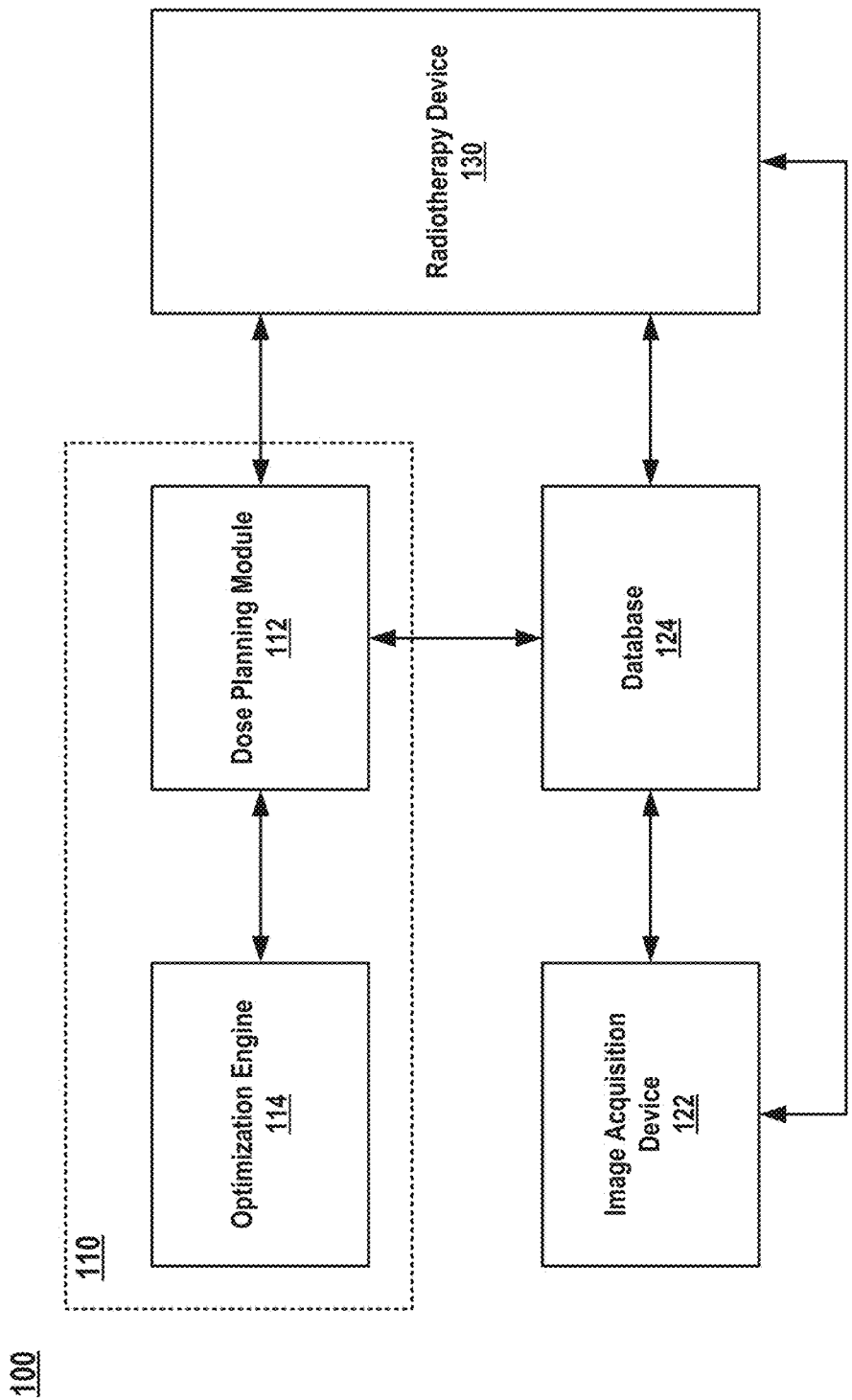
FIG. 2A illustrates an exemplary radiotherapy system, according to some embodiments of the present disclosure.

FIG. 2A illustrates an exemplary radiotherapy system 100, according to some embodiments of the present disclosure. Radiotherapy system 100 may include a dose planning module 112 for generating a dose application plan, an optimization engine 114 for fine-tuning the dose application plan, an image acquisition device 122 for acquiring one or more medical images of a patient, a database 124 for storing the medical images, dose application information, etc., and a radiotherapy device 130 for performing radiation treatment in accordance with the dose application plan.

As shown in FIG. 2A, dose planning module 112 may communicate with database 124 to receive planning data stored therein. The planning data may include patient specific information such as age, gender, tumor size, etc. The planning data may also include medical images such as Magnetic Resonance Imaging (MRI) images and Computed Tomography (CT) images of the patient showing internal structure of the anatomical portion under treatment.

The medical images may be provided by one or more image acquisition device 122, including the same or different devices. Image acquisition device 122 may include an MRI imaging device, a CT imaging device, or other medical imaging devices for obtaining one or more medical images of a patient. Image acquisition device 122 may provide the medical images to radiotherapy device 130 and/or database 124. In some embodiments, the medical images may be preprocessed by, for example, image acquisition device 122 to segment a target (e.g., a tumor). One or more OARs may also be segmented by image acquisition device 122. In these embodiments, image acquisition device 122 may provide the medical images as well as the segmentation information to database 124, and dose planning module 112 may receive the medical images and the segmentation information from database 124. In other embodiments, segmentation of the target and/or OARs may be performed by dose planning module 112. In these embodiments, image acquisition device 122 may provide the medical images to database 124, and dose planning module 112 may segment the medical images obtained from database 124.

The planning data stored in database 124 may be obtained from radiotherapy device 130. In some embodiments, the planning data may be collected from multiple radiotherapy devices, or retrieved from a remote location, such as a radiotherapy data repository or a data center. Dose planning module 112 may use the planning data to generate a dose application plan to be implemented by radiotherapy device 130 to deliver radiation treatment to a patient.

Dose planning module 112 may communicate with optimization engine 114 to perform dose plan optimization. For example, dose planning module may send an initial dose application plan to optimization engine 114. Optimization engine 114 may fine-tune the initial dose application plan to maximize the dose received by the target and minimize the dose received by the OARs. After optimization, the optimized dose application plan may be returned to dose planning module 112 and may be retrieved by radiotherapy device 130 to deliver treatment to a patient.

In some embodiments, dose planning module 112 and optimization engine 114 may be implemented in a single data processing device 110. For example, dose planning module 112 and optimization engine 114 may be implemented as different software programs operating on the same hardware device, as will be described in greater detail later with respect to FIG. 2C. In some embodiments, optimization engine may be embedded into dose planning module 112. For example, optimization engine 114 may be implemented as a sub-device of a dose planning device or a sub-routine of a dose planning software application. In some embodiments, dose planning module 112 and optimization engine 114 may be implemented as separate standalone modules.

In some embodiments, radiotherapy device 130 and dose planning module 112 may be located in the same medical facility. In some other embodiments, radiotherapy device 130 may be remote with respect to dose planning module 112 (e.g., located at different locations in the same or different medical facilities) and the data communication between radiotherapy device 130 and dose planning module 112 may be carried out through a network. The network may include an internal or external network (e.g., Internet). Similarly, dose planning module 112 and database 124, dose planning module 112 and optimization engine 114, database 124 and radiotherapy device 130, image acquisition device 122 and radiotherapy device 130, database 124 and image acquisition device 122 may also be located locally or remote to each other, and may communicate over an internal or external network.

Figure 2B:
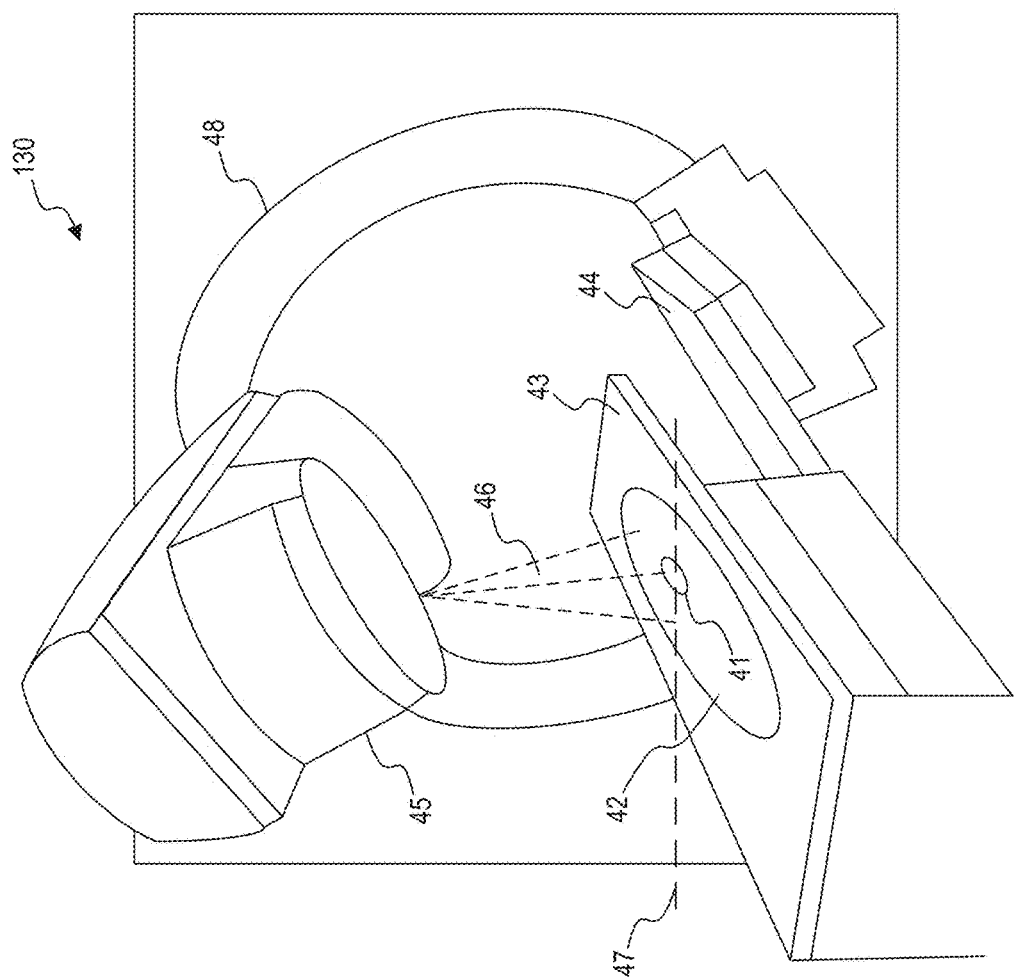
FIG. 2B illustrates an exemplary radiotherapy device, according to some embodiments of the present disclosure.

FIG. 2B illustrates an exemplary configuration of radiotherapy device 130 (e.g., a linear accelerator), according to some embodiments of the present disclosure. Using a linear accelerator 130, a patient 42 may be positioned on a patient table 43 to receive the radiation dose according to a dose application plan (e.g., determined by dose planning module 112 or further optimized by optimization engine 114). Linear accelerator 130 may include a radiation head 45 that generates a radiation beam 46. The entire radiation head 45 may be rotatable around a horizontal axis 47. In addition, below the patient table 43 there may be provided a flat panel scintillator detector 44, which may rotate synchronously with radiation head 45 around an isocenter 41. The intersection of the axis 47 with the center of the beam 46, produced by the radiation head 45, is usually referred to as the "isocenter". The patient table 43 may be motorized so that the patient 42 can be positioned with the tumor site at or close to the isocenter 41. The radiation head 45 may rotate about a gantry 48, to provide patient 42 with a plurality of varying dosages of radiation according to the dose application plan.

Figure 2C:
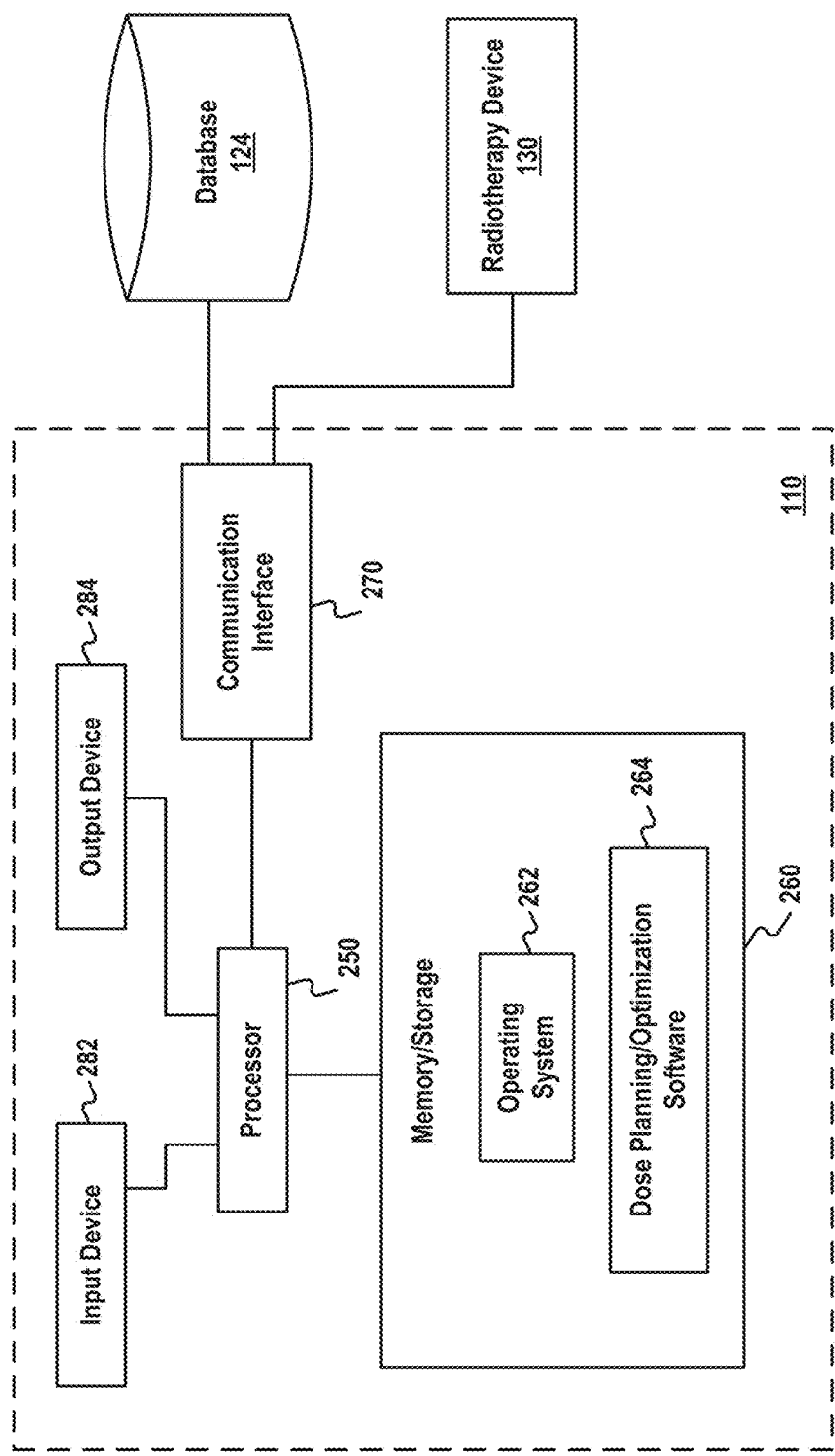
FIG. 2C illustrates an exemplary data processing device used in the radiotherapy system of FIG. 2A, according to some embodiments of the present disclosure.

FIG. 2C illustrates an exemplary data processing device 110. As shown in FIG. 2C, data processing device 110 may include a processor device 250, a memory or storage device 260, a communication interface 270, an input device 282, and an output device 284. Memory/storage device 260 may store computer executable instructions, such as operating system 262 and dose planning/optimization software 264. Processor device 250 may be coupled to memory/storage device 260 and configured to execute the computer executable instructions stored thereon. For example, processor device 250 may execute dose planning/optimization software 264 to implement functionalities of dose planning module 112 and/or optimization engine 114. Processor device 250 may communicate with database 124 through communication interface 270 to send/receive data to/from database 124. Although only one database 124 is shown in FIG. 2C, one skilled in the art would appreciate that database 124 may include a plurality of devices located either in a central or distributed manner.

Processor device 250 may include one or more general-purpose processing devices such as a microprocessor, central processing unit (CPU), or the like. More particularly, processor device 250 may be a complex instruction set computing (CISC) microprocessor, reduced instruction set computing (RISC) microprocessor, very long instruction Word (VLIW) microprocessor, a processor implementing other instruction sets, or processors implementing a combination of instruction sets. Processor device 250 may also be one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, processor device 250 may be a special-purpose processor, rather than a general-purpose processor.

Memory/storage device 260 may include a read-only memory (ROM), a flash memory, a random access memory (RAM), a static memory, etc. In some embodiments, memory/storage device 260 may include a machine-readable storage medium. While the machine-readable storage medium as an exemplary embodiment may be a single medium, the term "machine-readable storage medium" should be taken to include a single medium or multiple media (e.g., a centralized or distributed database, and/or associated caches and servers) that store one or more sets of instructions/data. The term "machine-readable storage medium" shall also be taken to include any medium that is capable of storing or encoding a set of instructions for execution by the machine and that cause the machine to perform any one or more of the methodologies of the present disclosure. The term "machine readable storage medium" shall accordingly be taken to include, but not be limited to, solid-state memories, and optical and magnetic media.

Communication interface 270 may include a network adaptor, a cable connector, a serial connector, a USB connector, a parallel connector, a high-speed data transmission adaptor such as fiber, USB 3.0, thunderbolt, etc., a wireless network adaptor such as WiFi adaptor, telecommunication (3G, 4G/LTE etc.) adaptor, etc. Communication interface 270 may also include communication interface with radiotherapy device 130. Processor device 250 may communicate with database 124, radiotherapy device 130, or other devices or systems via communication interface 270. Input device 282 may include a keyboard, a mouse, a touchscreen, or other suitable devices for receiving information input by a user. Output device 284 may include a display, a printer, or other suitable devices for outputting information to the user.

Data processing device 110 may be in communication with radiotherapy device 130. As noted above, radiotherapy device 130 may be a device configured to deliver radiation therapy. Radiotherapy device 130 may include a radiation source and employ a radiation beam shaper to control the shape and/or size of the radiation beam emitted by the radiation source.

Figure 3A:
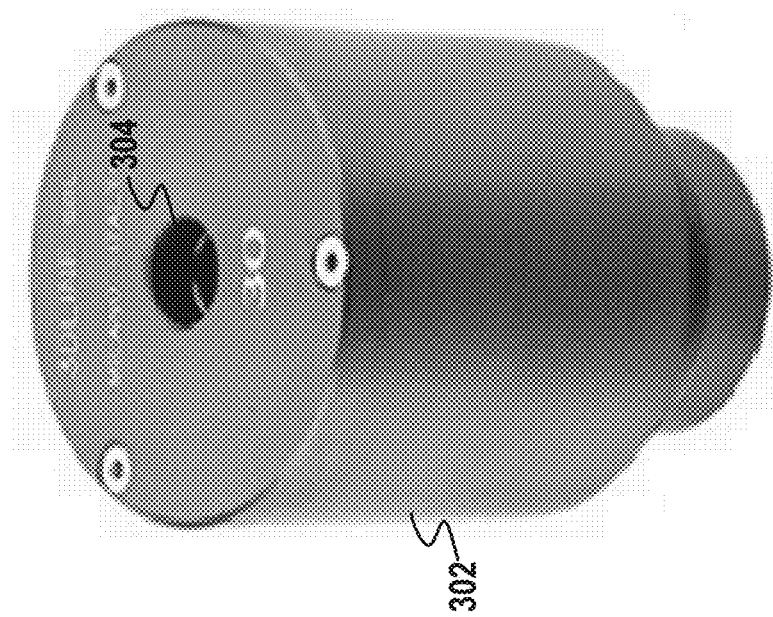
FIG. 3A illustrates an exemplary radiation beam shaper of the radiotherapy device, according to some embodiments of the present disclosure.

FIG. 3A illustrates an exemplary radiation beam shaper 302, according to some embodiments of the present disclosure. Radiation beam shaper 302 may be installed on a collimator 310 (e.g., shown in FIG. 3B) and towards patient 42. Radiation beam shaper 302 may include an opening 304 to allow passage of a radiation beam. Opening 304 may be a cone-shaped opening, which may be sized and shaped to generate a radiation beam having a cone-like shape. Radiation beam shaper 302 may be used to control the size of the radiation beam passing through opening 304. For example, radiation applied along each arc may employ a particular sized radiation beam, and the size of radiation beams applied along different arcs may be different. The radiation beam size may be controlled by switching radiation beam shapers having different opening sizes. In some embodiments, opening 304 may be less than 5 cm, or may be less than 1 cm in diameter. For example, opening 304 may be 1 mm-5 mm in diameter. Other sizes may also be used.

Figure 3B:
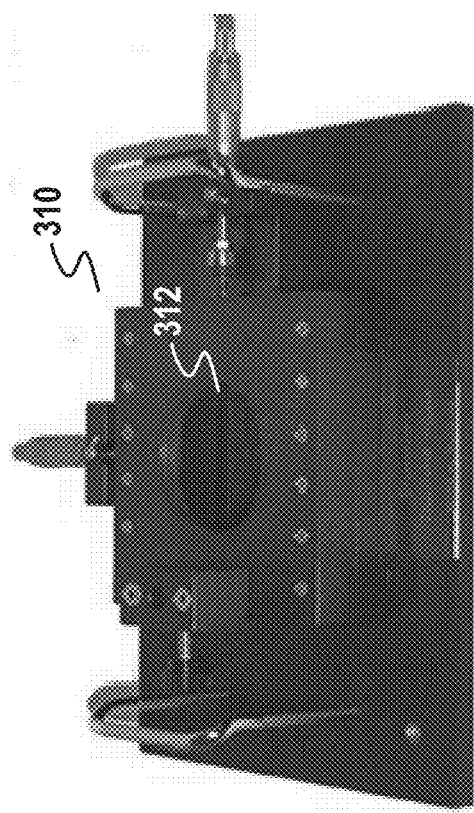
FIG. 3B illustrates an exemplary collimator of the radiotherapy device, according to some embodiments of the present disclosure.

FIG. 3B illustrates an exemplary collimator 310. Collimator 310 may include a mounting opening 312 through which a radiation beam shaper (e.g., 302) may be installed. For example, the radiation beam shaper may be installed onto collimator 310 through interlocking, fastening, screwing, snap-fitting, or other suitable method.

In a radiotherapy treatment, the dose planning stage can be divided into two parts. The first part may include the segmentation of a target, such as a tumor. In some embodiments, the first part may also include the segmentation of OARs. As noted above, the segmentation may be performed by image acquisition device 122 or by dose planning module 112. For example, image acquisition device 122 or dose planning module 112 may identify a target volume in a medical image by contouring the target in each 2D layer or slice of the medical image and combining the contours of multiple 2D layers or slices. Similarly, image acquisition device 122 or dose planning module 112 may identify an OAR volume in a medical image by contouring the OAR in each 2D layer or slice of the medical image and combining the contours of multiple 2D layers or slices. The segmentation of the target/OAR may be performed automatically or manually.

After the segmentation stage, the second part of the dose planning may include creating a dose application plan. The dose application plan may indicate the specific steps to apply radiation beams, normally from multiple angles, to the target under treatment. The dose application plan may include arc placement, dose rate, and/or radiation beam shape. The arc placement may indicate the positions or angles from which radiation is to be applied. The dose rate may indicate the desired amount of dose, normally measured by the beam-on time. The radiation beam shape may be controlled by a radiation beam shaper (e.g., 302).

Figure 4:
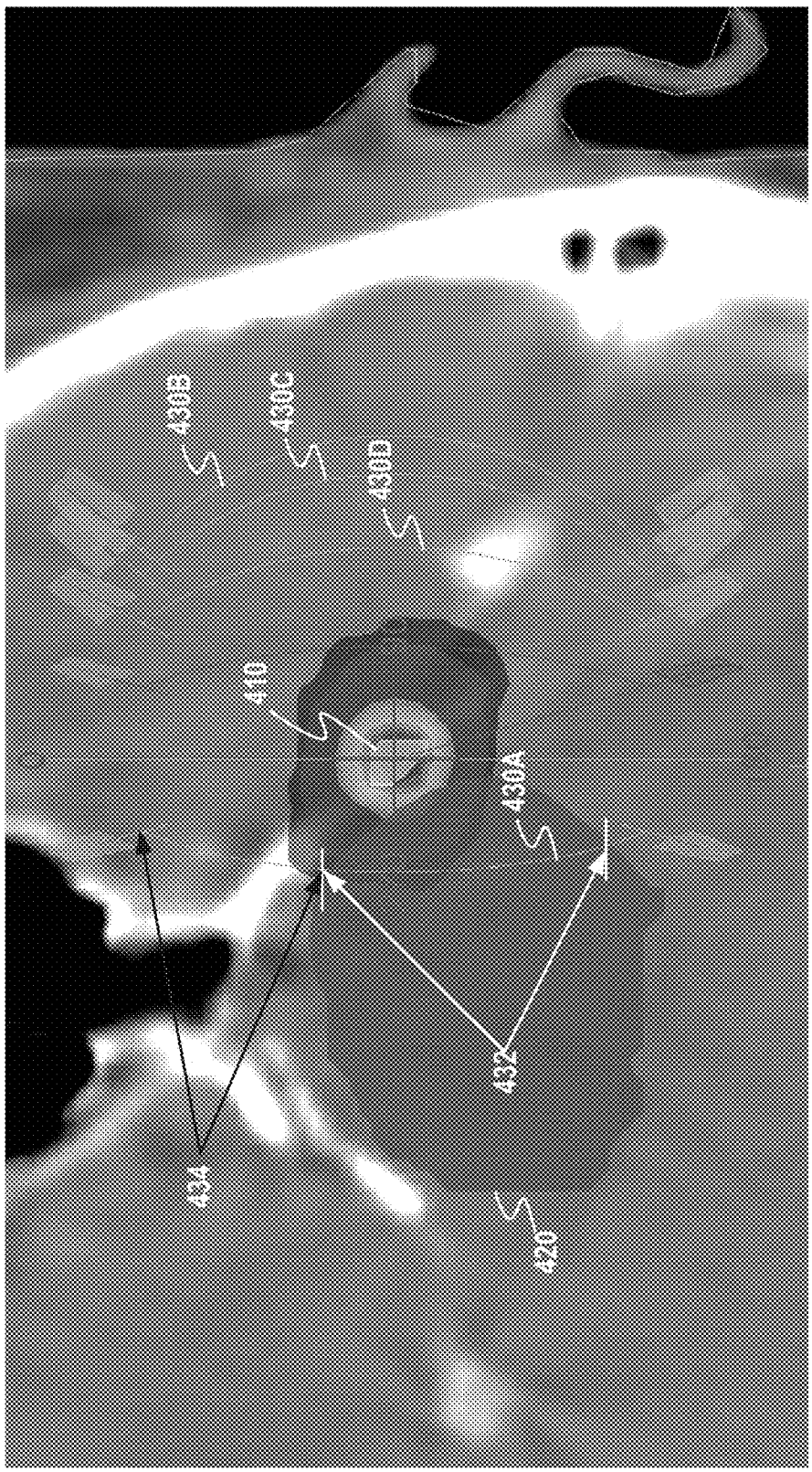
FIG. 4 illustrates an exemplary dose planning method with reference to a 2D medical image, according to some embodiments of the present disclosure.

FIG. 4 illustrates an exemplary dose planning method with reference to a 2D medical image. In FIG. 4, a target 410 and an OAR 420 may be segmented by image acquisition device 122 or dose planning module 112, as noted above. FIG. 4A shows multiple arcs, for example, 430A, 430B, 430C, and 430D, from which radiation may be applied. For example, radiation head 45 may rotate along arc 430A and apply radiation at one or more points along arc 430A. The placement of the arcs may be determined by dose planning module 112 based on the size and location of the target and/or the OAR, the desired dose to be received by the target, the dose constraint to be satisfied with respect to the OAR, and/or any other parameter known to one of ordinary skill in the art. In some embodiments, dose planning module 112 may determine the placement of the arcs, dose rate to be applied along each arc, and the radiation beam shape to be used on each arc. In some embodiments, dose planning module 112 may also determine a weighting factor associated with each arc. For example, in FIG. 4, arc 430A covers a portion of OAR 420. Dose planning module 112 may assign a weighting factor to arc 430A to reduce the dose received by OAR 420 when radiation is applied along arc 430A. Similarly, dose planning module 112 may assign a weighting factor to arc 430B to increase the dose received by target 410 when radiation is applied along arc 430B. In this manner, the dose applied to target 410 and OAR 420 can be controlled.

In some cases, the combination of arc placement, dose rate (as modified by weighting factors), and radiation beam shape may not be able to satisfy the dose constraint. For example, in the case shown in FIG. 4, a certain area in target 410 may not be able to receive enough dose if a weighting factor is assigned to arc 430A to satisfy the dose constraint imposed by OAR 420. On the other hand, if the weighting factor is increased to satisfy the dose requirement of target 410, the dose constraint imposed by OAR 420 may not be satisfied. In this case, dose planning module 112 may divide arc 430A into multiple segments and assign different dose rate to different segments. For example, dose planning module 112 may divide arc 430A into segment 432 and segment 434. In segment 432, the dose rate may be decreased to a lower level to reduce the radiation received by OAR 420. In segment 434, the dose rate may be increased to a higher level to satisfy the dose requirement of target 410. In this way, a dose application plan may be created to satisfy both the dose requirement of target 410 and dose constraint of OAR 420.

Once dose planning module 112 divides one or more arcs into multiple segments and assigns different dose rates (e.g., by assigning different weighting factors) to different segments, dose planning module 112 may then calculate a predicted OAR dose based on the assigned dose rate associated with each segment. For example, dose planning module 112 may calculate a dose distribution within the volume of target 410 and OAR 420 based on the arc placement, arc segments, dose rates, and radiation beam shape as determined in the dose application plan. The dose distribution may be calculated, for each voxel of target 410 or OAR 420, by summing up the dose received from each individual radiation beam prescribed by the dose application plan, taking into consideration the dose rate (e.g., weighting factor) associated with each arc segment and radiation beam shape associated with each arc segment. Dose planning module 112 may then compare the predicted OAR dose with the constraint on the OAR dose to determine whether the constraint is satisfied.

If the constraint is not satisfied, the dose planning module 112 may revise one or more parameters in the dose application plan. For example, dose planning module 112 may revise the arc placement by, for example, adding a new arc, removing an existing arc, changing the position, direction, length, and/or curvature of an arc, etc. Dose planning module 112 may also revise the segmentation of an arc. For example, dose planning module 112 may divide an arc into a different number of segments, assign a different length to a segment, etc. In addition, dose planning module 112 may revise the dose rate associated with each segment. For example, dose planning module 112 may increase or decrease the dose rate assigned to a segment. Moreover, dose planning module 112 may revise the radiation beam shape. For example, dose planning module 112 may assign a different beam shape to an arc or an arc segment. The different radiation beam shape, including the shape of the radiation beam and the size of the radiation beam, may be achieved by employing radiation beam shapers having openings of different shapes and/or sizes. The revision may be an iterative process, in which multiple rounds of revisions may be carried out by dose planning module 112 until the resulting dose application plan satisfies the constraint.

If the constraint is satisfied, then dose planning module 112 may provide the dose application plan with the determined placement of the arc, the arc segments, and the dose rate associated with each segments to radiotherapy device 130 for performing radiation treatment. In some embodiments, dose planning module 112 may provide the dose application plan to a user (e.g., physician, doctor, etc.) for further consideration.

In some embodiments, dose planning module 112 may provide the dose application plan to optimization engine 114 for optimization. The dose application plan determined by dose planning module 112 may be an initial plan that satisfies both the target dose requirement and the OAR dose constraints. Optimization engine 114 may fine-tune the initial plan and generate an optimized dose application plan. For example, optimization engine 114 may calculate predicted target dose and OAR dose using different arc placements, arc segmentations, and/or radiation beam shapes and compare the calculation results. In some embodiments, a plan having the lowest OAR dose may be selected as the optimized plan. In some embodiments, a plan having a balanced high target dose and low OAR dose may be selected as the optimized plan. In some embodiments, a plan having the highest target dose and satisfying the OAR dose constraint may be selected as the optimized plan. A person skilled in the art will understand that other criteria may also be adopted in the selection of the optimized plan. Once the optimized plan is finalized, the plan may be retrieved or sent to radiotherapy device 130 for implementation.

Figure 5:
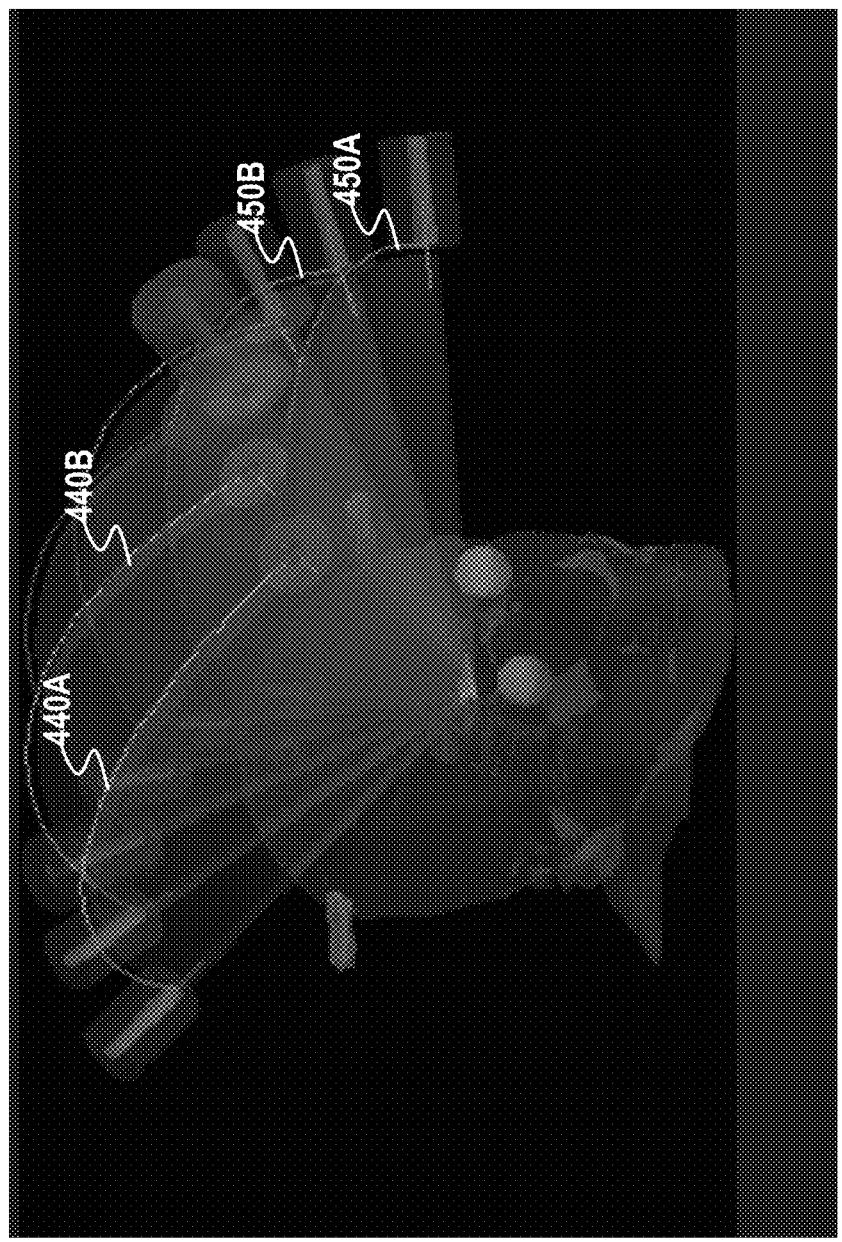
FIG. 5 illustrates an exemplary dose planning method with reference to a 3D medical image, according to some embodiments of the present disclosure.

FIG. 5 illustrates an exemplary dose planning method with reference to a 3D medical image. In FIG. 5, the directions along which arcs 440A and 450A may be different. This may be achieved by rotating patient table 43. For example, radiation head 45 may apply radiation along arcs 440A and 440B while patient table 43 is at a first position, and may apply radiation along arcs 450A and 450B while patient table 43 rotates to a second position. The rotation of patient table 43 may also be considered as a parameter in determining arc placement and/or arc segmentation. For example, dose planning module 112 may generate a dose application plan having arcs extending along different directions, and divide one or more arcs into multiple segments and assign individual dose rate to each segment.

Figure 6:
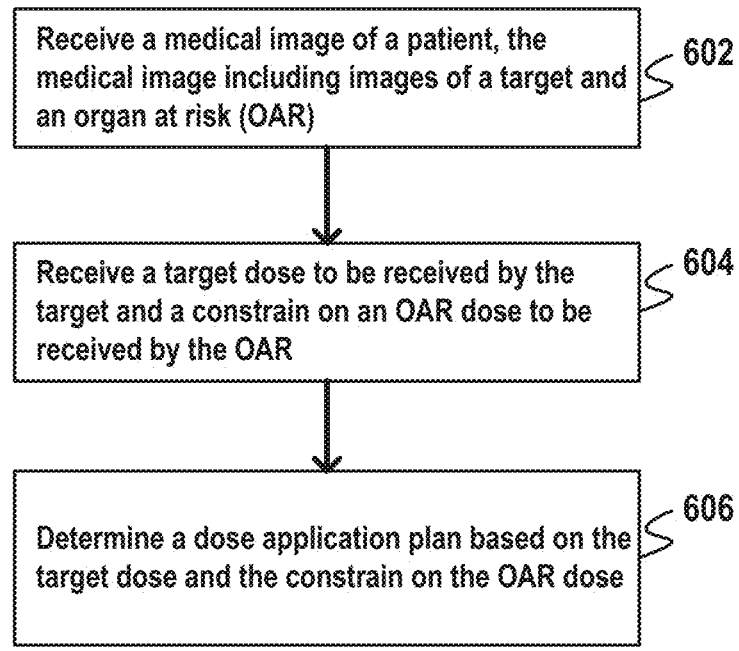
FIG. 6 is a flowchart of an exemplary dose planning method, according to some embodiments of the present disclosure.

FIG. 6 is a flowchart of an exemplary dose planning method 600, according to some embodiments of the present disclosure. At step 602, dose planning module 112 may receive a medical image (e.g., the medical image shown in FIG. 4) of a patient from database 124. The medical image may be generated by image acquisition device 122 and may include images of a target (e.g., target 410) and an OAR (e.g., OAR 420).

At step 604, dose planning module 112 may receive a target dose to be received by target 410 and a constraint on an OAR dose to be received by OAR 420. The target dose and the constraint on the OAR dose may be received from a user inputted through input device 282.

At step 606, dose planning module 112 may determine a dose application plan based on the target dose and the constraint on the OAR dose. Step 606 is described in greater detail in FIG. 7.

Figure 7:
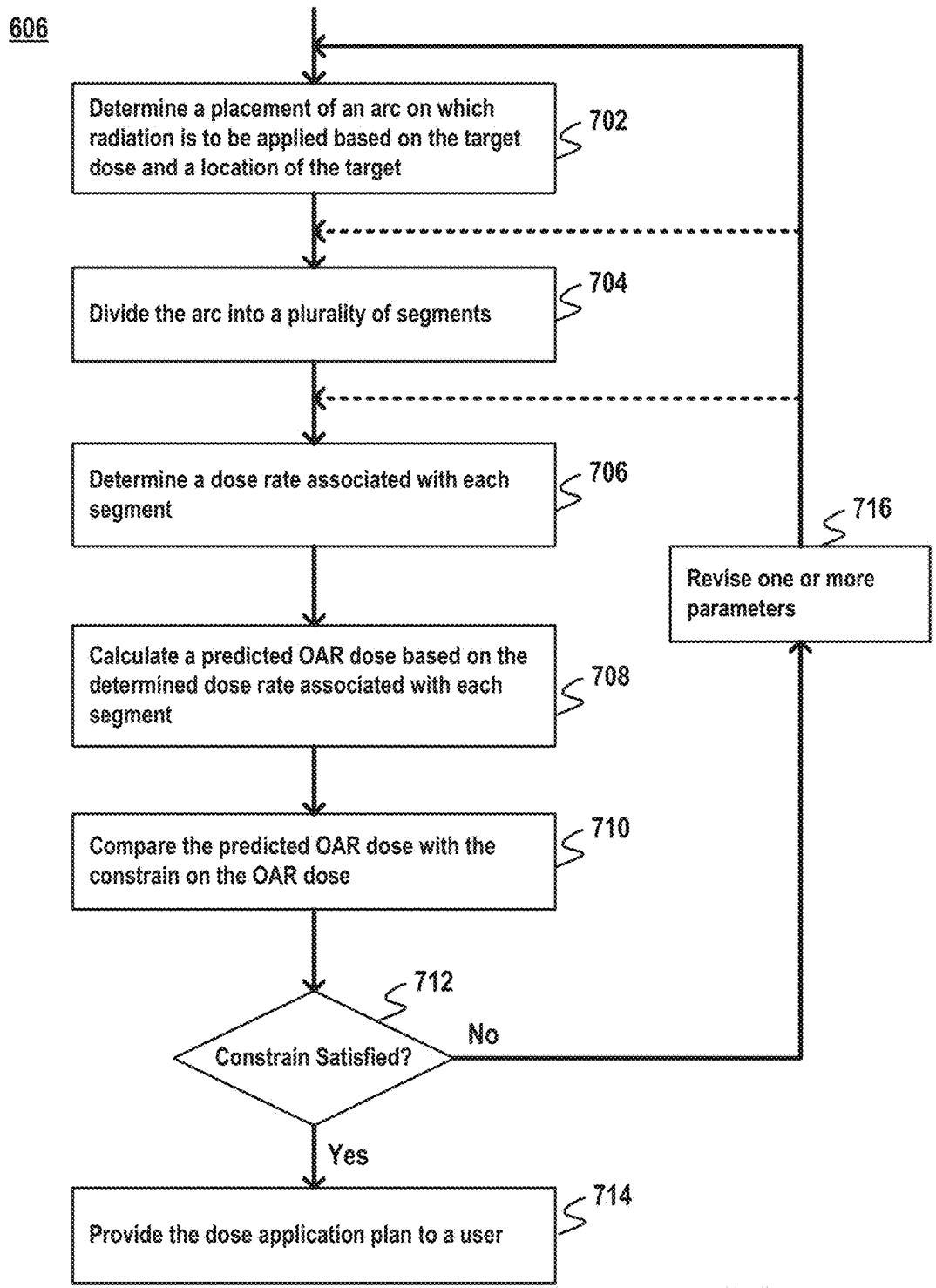
FIG. 7 is a flowchart of an exemplary subroutine of the dose planning method of FIG. 6, according to some embodiments of the present disclosure.

Referring to FIG. 7, step 606 may include a substep 702, in which dose planning module 112 and/or a user may determine a placement of an arc on which radiation is to be applied based on the target dose and a location of the target. For example, in some embodiments, a user may determine placement of arcs 430A, 430B, 430C, and 430D such that radiation head 45 may rotate along these arc to apply radiation. In some embodiments, dose planning module 112 may determine placement of these arcs. At substep 704, dose planning module 112 may divide one or more arcs, such as arc 430A, into a plurality of segments, such as segments 432 and 434. At substep 706, dose planning module 112 may determine a dose rate associated with each arc or arc segment. For example, each arc segment may be assigned an individual dose rate and different arc segments, even on the same arc, may be assigned different dose rates. At substep 708, dose planning module 112 may calculate a predicted OAR dose based on the determined dose rate associated with each arc or arc segment. For example, dose planning module 112 may calculate an individual OAR dose resulting from each individual arc or arc segment and sum up the individual OAR dose to arrive at a predicted OAR dose. At substep 710, dose planning module 112 may compare the predicted OAR dose and the constraint on the OAR dose to check if the dose application plan satisfy the constraint (at substep 712). If the constraint is satisfied, process proceeds to substep 714, in which dose planning module 112 may provide the dose application plan to a user for further consideration. In some embodiments, dose planning module 112 may also provide the dose application plan to radiotherapy device 130 for performing radiation treatment. If the constraint is not satisfied, process proceeds to substep 716, in which dose planning module 112 may revise one or more parameters such as the arc placement, the segmentation of an arc, and/or the dose rate associated with each arc segment. Accordingly, process may proceeds to any one of substep 702, 704, or 706.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present invention also relates to a system for performing the operations herein. This system may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMS), EPROMs, EEPROMs, magnetic or optical cards, or any type of media suitable for storing electronic instructions, each coupled to a computer system bus.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with compute executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A system for generating a dose application plan for radiotherapy, comprising:
    a memory storing computer executable instructions;
    a processor device communicatively coupled to the memory, wherein the processor device is configured to execute the computer executable instructions for:
        receiving a target dose for treating a target during a radiotherapy treatment;
        determining a placement of an arc along which radiation is to be applied based on the target dose and a location of the target;
        dividing the arc into a plurality of segments;
        determining a dose rate associated with each segment;
        calculating a predicted dose to be received by an organ at risk (OAR) based on the determined dose rate associated with each segment; and
        generating the dose application plan based on the predicted dose and the dose rate associated with each segment.

2. The system of claim 1, wherein the processor device is configured to execute the computer executable instructions for:
    receiving a constraint on a dose to be received by the OAR during the radiotherapy treatment; and
    comparing the predicted dose with the constraint to determine whether the predicted dose satisfies the constraint.

3. The system of claim 2, wherein the processor device is configured to execute the computer executable instructions for:
    providing the dose application plan with the determined placement of the arc, the plurality of segments of the arc, and the dose rate associated with each segment to a user when the predicted dose satisfies the constraint.

4. The system of claim 2, wherein the processor device is configured to execute the computer executable instructions for:
    revising at least one of: the placement of the arc, the dividing of the plurality of segments, or the dose rate when the predicted dose does not satisfy the constraint.

5. The system of claim 1, wherein the processor device is configured to execute the computer executable instructions for:
    determining a radiation beam shape associated with the arc; and
    calculating the predicted dose to be received by the OAR based on the determined dose rate associated with each segment and the radiation beam shape associated with the arc.

6. The system of claim 5, comprising:
    a radiation beam shaper to control the radiation beam shape associated with the arc.

7. The system of claim 6, wherein the radiation beam shaper has a cone-shaped opening.

8. The system of claim 6, wherein the radiation beam shaper has an opening that is less than 5 cm in size.

9. The system of claim 1, wherein the processor device is configured to execute the computer executable instructions for:
    determining placement of a plurality of arcs along which radiation is to be applied based on the target dose and the location of the target; and
    determining a weighting factor associated with each arc.

10. The system of claim 1, wherein the processor device is configured to execute the computer executable instructions for:
    receiving a medical image of a patient, the medical image including images of the target and the OAR; and
    identifying a target volume corresponding to the target and an OAR volume corresponding to the OAR in the medical image.

11. A method for dose planning in a radiotherapy system, the method comprising:
    receiving a target dose for treating a target during a radiotherapy treatment;
    determining a placement of an arc along which radiation is to be applied based on the target dose and a location of the target;
    dividing the arc into a plurality of segments;
    determining a dose rate associated with each segment;
    calculating a predicted dose to be received by an organ at risk (OAR) based on the determined dose rate associated with each segment; and
    generating a dose application plan based on the predicted dose and the dose rate associated with each segment.

12. The method of claim 11, comprising:
    receiving a constraint on a dose to be received by the OAR during the radiotherapy treatment; and
    comparing the predicted dose with the constraint to determine whether the predicted dose satisfies the constraint.

13. The method of claim 12, comprising:
    providing the dose application plan with the determined placement of the arc, the plurality of segments of the arc, and the dose rate associated with each segments to a user when the predicted dose satisfies the constraint.

14. The method of claim 12, comprising:
    revising at least one of: the placement of the arc, the dividing of the plurality of segments, or the dose rate when the predicted dose does not satisfy the constraint.

15. The method of claim 11, comprising:
    determining a radiation beam shape associated with the arc; and
    calculating the predicted dose to be received by the OAR based on the determined dose rate associated with each segment and the radiation beam shape associated with the arc.

16. The method of claim 14, comprising:
    controlling, using a radiation beam shaper, the radiation beam shape associated with the arc.

17. The method of claim 11, comprising:
    determining placement of a plurality of arcs along which radiation is to be applied based on the target dose and the location of the target; and
    determining a weighting factor associated with each arc.

18. The method of claim 11, comprising:
    receiving a medical image of a patient, the medical image including images of the target and the OAR; and
    identifying a target volume corresponding to the target and an OAR volume corresponding to the OAR in the medical image.

19. A non-transitory computer-readable medium storing non-transitory instructions for generating a dose application plan for radiotherapy, wherein the instructions, when executed by a processor device, cause the processor device to perform a method including:
  receiving a target dose for treating a target during a radiotherapy treatment;
  determining a placement of an arc along which radiation is to be applied based on the target dose and a location of the target;
  dividing the arc into a plurality of segments;
  determining a dose rate associated with each segment;
  calculating a predicted dose to be received by an organ at risk (OAR) based on the determined dose rate associated with each segment; and
  generating the dose application plan based on the predicted dose and the dose rate associated with each segment.

20. The non-transitory computer-readable medium of claim 19, wherein the instructions stored thereon, when executed by the processor device, cause the processor device to perform:
  receiving a constraint on a dose to be received by the OAR during the radiotherapy treatment;
  comparing the predicted dose with the constraint to determine whether the predicted dose satisfies the constraint;
  providing the dose application plan with the determined placement of the arc, the plurality of segments of the arc, and the dose rate associated with each segments to a user when the predicted dose satisfies the constraint; and
  revising at least one of: the placement of the arc, the dividing of the plurality of segments, or the dose rate when the predicted dose does not satisfy the constraint.

* * * * *

UNITED STATES PATENT AND TRADEMARK OFFICE
CERTIFICATE OF CORRECTION

PATENT NO. : 10,238,893 B2
APPLICATION NO. : 15/485204
DATED : March 26, 2019
INVENTOR(S) : Brett Mathew Sloman Page 1 of 1

It is certified that error appears in the above-identified patent and that said Letters Patent is hereby corrected as shown below:

In the Claims

In Column 12, Line 51, in Claim 25, delete "claim 14," and insert --claim 15,-- therefor Signed and Sealed this
Twenty-third Day of July, 2019

Andrei Iancu
*Director of the United States Patent and Trademark Office*